Jan. 17, 1961 C. G. KLEHM Plant Pat. 2,011

PEONY PLANT

Filed Sept. 30, 1959

Inventor
Carl G. Klehm
By Hofgren, Brady,
Wegner, Allen & Stellman
Attorneys

United States Patent Office

Plant Pat. 2,011
Patented Jan. 17, 1961

2,011

PEONY PLANT

Carl G. Klehm, 3 E. Algonquin, Arlington Heights, Ill.

Filed Sept. 30, 1959, Ser. No. 843,596

1 Claim. (Cl. 47—60)

Figure 1:
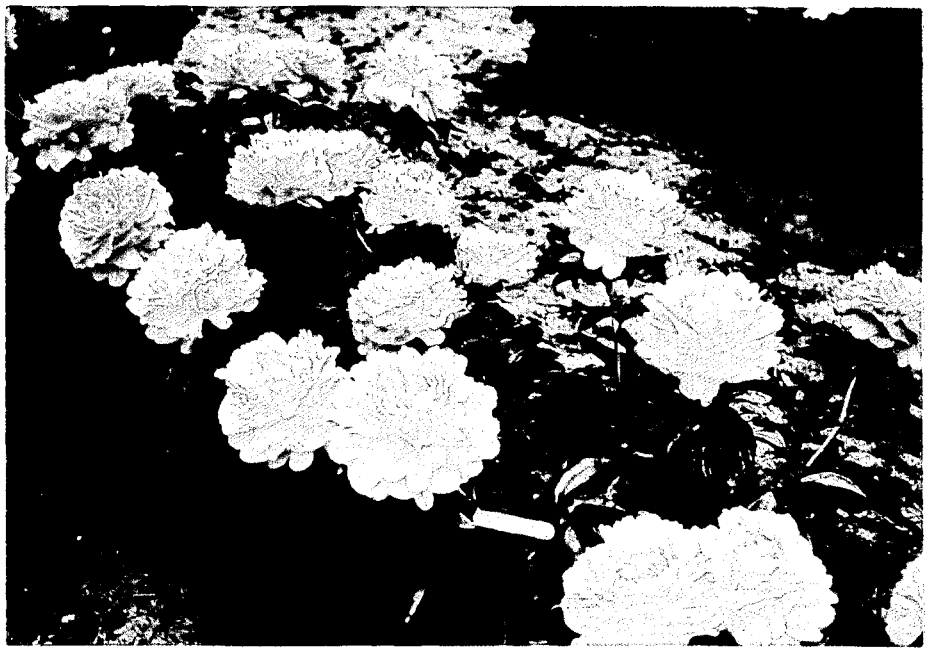
Figure 2:
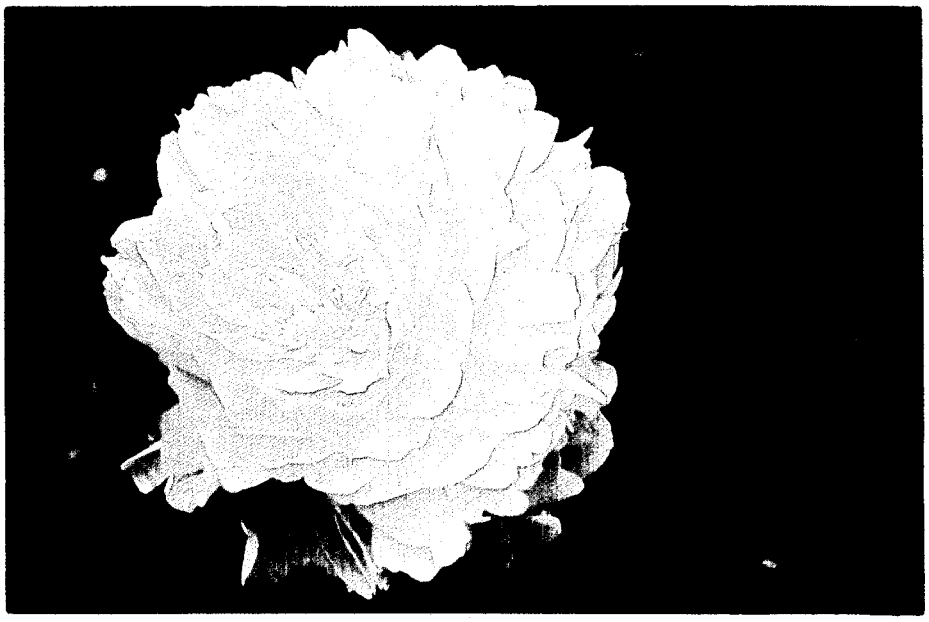

The present invention relates to a new variety of and strain of peony plant; the novel characteristics reside particularly in the extreme large size of the bloom, the unusual color of the strain, the robustness of the plant and its outstanding keeping qualities, both in the field and as a cut bloom.

This peony plant was originated by me at my nursery in Arlington Heights, Illinois, from a cross between Mr. Van Leeuwan, the pollen parent (not patented); and Mons. Jules Elie, the seed parent (not patented); by the processes of handling pollenization. This peony plant was asexually reproduced by me in Arlington Heights, Illinois, by root division. Thousands of seedlings were developed as a result of this cross and from these thousands this particular peony plant was selected. It took seven years for the plant to produce its first bloom. The first bloom of the plant has been under constant observation for fourteen years.

The peony plant derives its outstanding dark green foliage, exceptional resistance to bacterial diseases, strength of stem and vigorous growth properties from its seed parent, Mons. Jules Elie. It derives its outstanding color characteristics and form of flower from its pollen parent, Mr. L. Van Leeuwan.

The peony plant forming the subject matter of this application is considered novel with respect to heartiness, size, health, rich dark green color of foliage, color of flower, non-lanceolated guard petals, and resistance to disease.

It is a marked characteristic of this peony plant that the full open bloom is extremely large, being 9¾″ in diameter, under normal growth conditions. It has a full, double rose-type bloom with absolutely no stamens or carpels. It is American Beauty Red in coloring, tipped with Silver on the edges of the petals.

This peony plant is suitable for garden growing and the bloom is exceptional as a cut flower, due particularly to its keeping qualities.

The accompanying drawing shows a typical specimen plant of the new variety, and a view of an individual flower, both being shown in color as nearly true as reasonably possible in a color illustration of this character.

As a convenient summary, the following detailed description of this new peony plant is given with color terminology generally in accordance with Maerz and Paul's "Dictionary of Color" except where general color terms are used:

Parentage:

*Seed Parent.*—Mons. Jules Elie, from which this new variety obtains its outstanding dark green foliage that is extremely resistant to bacterial diseases; the exceptional supporting strength of the stem, and the vigorous growth qualities of the plant.

*Pollen Parents.*—Mr. L. Van Leeuwan, from which this variety obtains its outstanding characteristics of color and form of flower.

*Flower*

Blooming habit: Annually.

Bud:

*Size.*—Very large.

*Form.*—Smooth, even and round.

*Color.*—American Beauty Red; Plate 3, K–8 on page 29.

*Sepals.*—Smooth green wrapped tightly around bud.

*Calyx.*—Polysepalous.

*Peduncle.*—None.

*Opening.*—Unfailing opening qualities—a very dependable performer.

Bloom:

*Size.*—Very large, average size when fully expanded 9¾″ under normal growth conditions.

*Borne.*—Singly, one main flower bud per stem with 3 to 4 auxiliary buds.

*Stems.*—Long, strong, approximately 33″ in height.

*Form.*—Rose type with 3 to 4 rows of guard petals.

*Petalage.*—Very double.

*Color.*—American Beauty Red, Plate 3, K–8 on page 29; with silver-tipped petal edges.

*Variegations.*—None.

*Discoloration.*—Under intense direct hot sun, a slight fading of color will occur after three days.

Petals:

*Texture.*—Thick, not affected by wet or hot weather.

*Appearance.*—Inside and outside, satiny.

*Form.*—Smooth—not lanceolated.

*Arrangement.*—Imbricated (double), many petaloids in center.

*Persistence.*—Drop off cleanly.

*Fragrance.*—Mildly scented.

*Lastingness.*—On the plant, very long; as a cut flower, very outstanding.

Genital organs:

*Stamens, anthers.*—None.

*Stamens, filaments.*—None, complete petalody.

*Pollen.*—None, complete petalody.

*Styles.*—None, complete petalody.

*Stigmas.*—None, complete petalody.

*Ovaries.*—None, complete petalody.

Fruit: None, complete petalody.

*Plant*

Form: Bush.

Growth: Vigorous, strong.

Foliage:

*Leaflets.*—Five.

*Size.*—Medium.

*Quantity.*—Above normal.

*Color.*—Normal rich dark green, of lactiflord type, beginning approximately 5″ from ground and extending to bloom.

*Shape.*—Elliptically acute.

*Texture.*—Upper side, glossy with pronounced veins, underside, smooth with pronounced veins.

*Edge.*—Smooth

*Serration.*—None.

*Leaf stem.*—Color—normal medium green.

*Stipules.*—None.

*Disease resistance.*—Exceptionally resistant to leaf blotch as observed for several years at Arlington Heights, Illinois. This was observed during the blooming season and in the fall of the year with notations of these observations being kept in a book used for this purpose.

I claim:

A new and distinct variety of peony plant characterized by its extremely large size of bloom, its distinct color, and the robust heartiness of the plant as shown and described herein.

No references cited.